United States Patent
Tang Ee Ho et al.

(10) Patent No.: US 10,314,996 B2
(45) Date of Patent: Jun. 11, 2019

(54) MASK PACKAGE APPARATUS INTEGRATED WITH MASK SIZING RULER

(71) Applicant: Innosparks Pte Ltd, Singapore (SG)

(72) Inventors: Gareth Tang Ee Ho, Singapore (SG); Jiang Sak Kwok, Singapore (SG); Jerome Lee Wei Liang, Singapore (SG)

(73) Assignee: INNOSPARKS PTE LTD, Singapore (SG)

( * ) Notice: Subject to any disclaimer, the term of this patent is extended or adjusted under 35 U.S.C. 154(b) by 201 days.

(21) Appl. No.: 15/502,609

(22) PCT Filed: Aug. 25, 2014

(86) PCT No.: PCT/SG2014/000398
§ 371 (c)(1),
(2) Date: Feb. 8, 2017

(87) PCT Pub. No.: WO2016/032393
PCT Pub. Date: Mar. 3, 2016

(65) Prior Publication Data
US 2017/0274166 A1    Sep. 28, 2017

(51) Int. Cl.
*A61B 5/107*    (2006.01)
*A61M 16/06*    (2006.01)
(Continued)

(52) U.S. Cl.
CPC ....... *A61M 16/0605* (2014.02); *A61B 5/1072* (2013.01); *A61B 5/1075* (2013.01);
(Continued)

(58) Field of Classification Search
CPC .............. A61M 16/06; A61M 16/0605; A61M 2016/0661; A61M 2207/00;
(Continued)

(56) References Cited

U.S. PATENT DOCUMENTS 2,893,546 A * 7/1959 Kendall et al. ........ B65D 85/18
206/278
4,887,717 A * 12/1989 Secrest, Jr. ............ B65D 81/36
206/575
(Continued)

FOREIGN PATENT DOCUMENTS

SU    510221 A * 6/1976 ............... A41H 1/00
WO    2013088293 A1    6/2013
WO    2013118034 A1    8/2013

OTHER PUBLICATIONS

International Search Report for corresponding application PCT/SG2014/000398 filed Aug. 25, 2014; dated Jun. 22, 2015.
(Continued)

*Primary Examiner* — George B Bennett
(74) *Attorney, Agent, or Firm* — Cantor Colburn LLP

(57) ABSTRACT

A facemask package integrated with a mask sizing ruler is disclosed. The package stores the masks of various sizes. The mask sizing ruler comprising a first measuring gauge element, a second measuring gauge element and one or more sizes indicated thereon. The sizes in the sizing ruler are determined by categorizing one or more precisely previously measured distance from at least two points on one or more human faces into one or more sizes based on at least one distance on one or more masks of one or more mask sizes. At least one distance on one or more masks of one or more mask sizes is proportional to the maximum vertical distance of the mask in unfolded state. A system and method for determining the sizes indicated on the mask ruler are also disclosed.

15 Claims, 6 Drawing Sheets

(51) Int. Cl.
*A62B 23/02* (2006.01)
*G01B 3/38* (2006.01)
*A62B 18/02* (2006.01)
*G01B 3/02* (2006.01)
*G01B 3/28* (2006.01)

(52) U.S. Cl.
CPC .............. *A62B 23/025* (2013.01); *G01B 3/38* (2013.01); *A61M 16/06* (2013.01); *A61M 2016/0661* (2013.01); *A61M 2207/00* (2013.01); *A61M 2209/06* (2013.01); *A62B 18/02* (2013.01); *G01B 3/02* (2013.01); *G01B 3/28* (2013.01)

(58) Field of Classification Search
CPC .. A61M 2209/06; A61B 5/1072; A61B 5/107; A62B 18/02; A62B 23/025; G01B 3/02; G01B 3/28; G01B 3/38
USPC .................................................. 33/511, 512
See application file for complete search history.

(56) References Cited

U.S. PATENT DOCUMENTS

| | | | |
|---|---|---|---|
| 5,584,125 A | 12/1996 | Prete | |
| 6,728,589 B1* | 4/2004 | Delache et al. | A61M 16/06 128/206.21 |
| 7,672,973 B2* | 3/2010 | Lordo | A61M 16/06 707/803 |
| 7,827,038 B2* | 11/2010 | Richard et al. | A61M 16/06 705/2 |
| 8,351,711 B2* | 1/2013 | Takano et al. | G06K 9/00268 382/118 |
| 9,307,930 B2* | 4/2016 | Todd | A61B 5/1075 |
| 9,361,411 B2* | 6/2016 | Thiruvengada et al. | G06F 17/5009 |
| 10,029,061 B2* | 7/2018 | Grashow | A61B 5/1077 |
| 2005/0022708 A1 | 2/2005 | Lee | |
| 2005/0181323 A1 | 8/2005 | Lauciello | |
| 2008/0060652 A1 | 3/2008 | Selvarajan | |
| 2008/0078396 A1 | 4/2008 | Janbakhsh | |
| 2010/0230314 A1 | 9/2010 | Lordo | |
| 2015/0191299 A1* | 7/2015 | Tsuei | B65D 85/07 206/494 |

OTHER PUBLICATIONS

Response to Written Opinion of the International Searching Authority for corresponding application PCT/SG2014/000398 filed Aug. 25, 2014; Response dated Jun. 23, 2016.
Written Opinion of the International Searching Authority for corresponding application PCT/SG2014/000398 filed Aug. 25, 2014; dated Jun. 22, 2015.
European Search Report for corresponding application EP 14 900 431.9; Report dated Jun. 22, 2018.
Resmed, "Mask Information Guide", May 30, 2011, pp. 1-30, XP055429801, Retrieved from the Internet: URL: https://www.resmed.com/ap/dam/documents/articles/bulletins/mask-bulletins/1014219-MaskInfoGuideAPACANZ.pdf.

* cited by examiner

MASK PACKAGE APPARATUS INTEGRATED WITH MASK SIZING RULER

CROSS REFERENCE TO RELATED APPLICATION

This application is a U.S. National Phase application under 35 U.S.C. § 371 of International Application No. PCT/SG2014/000398, filed on 25 Aug. 2014, the contents of which are herein incorporated by reference in their entirety.

TECHNICAL FIELD

The present disclosure relates generally to respiratory devices.

BACKGROUND

Facemasks or respirators are widely used to protect the user from inhaling dust or chemical particles, depending on the filter properties and certifications. The facemask comes in different sizes to suit the users of different facial geometry. For example, the mask sizes can be generalized as small, medium and large. For effective working of the mask, any gaps or loose fits of the mask on a human face should be avoided, when worn. The proper fit of the mask on the user face is obtained by selecting an appropriate size of the mask. To determine the appropriate size for a user, normally each size is tried on the user face and the appropriate size that suits the user face geometry is then determined. This is time consuming. To overcome this, many mask sizing gauges have been developed to easily determine the most appropriate size of the mask for a user.

WIPO Patent Application Number: WO 2013118034 discloses a sizing gauge that is structured to be used with a patient and is structured to enable an identification of a particular patient interface that is most appropriately sized for the patient. The sizing gauge includes a support portion and a sizing portion. The sizing portion includes a first gauge element and a plurality of second gauge elements. The first gauge element is disposed on the support portion and is structured to be positioned at a first location on the patient's face. The plurality of second gauge elements are disposed on the support portion and are situated at locations spaced from the first gauge element. The distance between the first gauge element and each second gauge element is representative of a size in one direction of each of at least some of the plurality of patient interfaces. At least one of the plurality of second gauge elements comprises a tactile feature.

U.S. Pat. No. 5,584,125 disclose a sizing guide for assisting in the initial determination of an appropriate size of respirator mask for a user thereof. The sizing guide has at least a first sizing gap having a known width such that comparison of the width of the first sizing gap with the length between a pair of facial landmarks such as the sellion landmark and the menton landmark provides an initial determination of the appropriate size respirator mask for the user which can then be fit tested. Preferably, the sizing guide also has a second sizing gap having a known width different from the width of the first sizing gap.

In above prior arts, the sizing gap or distance of the gauge element is compared with the length between a pair of facial landmarks. The gap or the measuring distance for each size in the gauge corresponds to at least one vertical distance at two points on each mask of various sizes. The sizes indicated on the gauge are obtained based on the dimensions of masks of various sizes.

SUMMARY

The following summary is provided to facilitate an understanding of some of the innovative features unique to the disclosed embodiment and is not intended to be a full description. A full appreciation of the various aspects of the embodiments disclosed herein can be gained by taking into consideration the entire specification, claims, drawings, and abstract as a whole.

One technical problem is how to produce a mask package that is integrated with a mask ruler for precisely determining the size of the mask that most suits a user, to overcome the above drawbacks.

The prior art systems do not analyze the measured facial geometries of various human faces to determine the optimal distances of the sizes to be indicated on the mask sizing gauge. Hence, the sizes determined by the prior art gauges may not be appropriate for the user. Further, the prior art gauges come as individual units and does not come along with the mask package and hence should be purchased separately. In addition, some mask packages recommend an age range for the various sizes, but there may be a wide range of facial profiles even within the age group, and the sizes may not fit all within the age group.

One technical solution is categorizing the facial dimensions of various users based on dimensions of the masks of various sizes.

It is, therefore, one embodiment of the disclosed embodiments to provide for a facemask package integrated with at least one mask sizing ruler. The package comprises one or more masks of one or more mask sizes and the mask sizing ruler. The mask sizing ruler has a first measuring gauge element, a second measuring gauge element and one or more sizes indicated on the ruler. The sizes in the sizing ruler are determined by categorizing one or more precisely previously measured distances from at least two points on one or more human faces into one or more sizes based on at least one distance on one or more masks of one or more mask sizes.

It is, therefore, one embodiment of the disclosed embodiments to provide for a facemask package integrated with at least one mask sizing ruler in which the second measuring gauge element has one or more size indicating portions to indicate one or more sizes.

It is, therefore, one embodiment of the disclosed embodiments to provide for a facemask package integrated with at least one mask sizing ruler in which the first and second gauge elements are used to indicate an appropriate size of a user by placing the mask sizing ruler on the user face and reading the appropriate size at the top. The size can be determined by the user using a mirror, or by another observer assisting the user to determine the correct size.

It is, therefore, one embodiment of the disclosed embodiments to provide for a facemask package integrated with at least one mask sizing ruler in which the two points utilized for determining the sizes indicated on the sizing ruler are selected from at least an eye level, bottom of a chin (menton landmark), a nose bridge, at least one cheek, an end of a lip and a center of a cheek.

It is, therefore, one embodiment of the disclosed embodiments to provide for a facemask package integrated with at least one mask sizing ruler in which the mask sizing ruler measures the size at the top, at the second gauge element.

It is, therefore, one embodiment of the disclosed embodiments to provide for a facemask package integrated with at least one mask sizing ruler in which the first gauge element is placed at menton landmark of the face, which is the bottom of the chin.

It is, therefore, one embodiment of the disclosed embodiments to provide for a facemask package integrated with at least one mask sizing ruler in which the second gauge element is placed at one of the two points except menton landmark, for example an eye level. The second gauge element placed at the eye level corresponds to a size indicated on the sizing ruler.

It is, therefore, one embodiment of the disclosed embodiments to provide for a facemask package integrated with at least one mask sizing ruler in which one or more distances of one or more mask sizes corresponds to maximum vertical distance on the mask in folded or unfolded state.

It is, therefore, one embodiment of the disclosed embodiments to provide for a system of determining one or more sizes indicated on a mask sizing ruler comprising an imaging device for scanning one or more faces to obtain one or more images and precisely measuring one or more distances of at least two points on one or more images, a storage device for storing the precisely measured one or more distances, a processing unit for processing the distance to categorize one or more precisely measured distances based on one or more distances of masks of one or more sizes and a determination unit for determining one or more sizes to be indicated on the mask sizing ruler based on categorized one or more precisely measured distances.

It is, therefore, one embodiment of the disclosed embodiments to provide for a method of determining one or more sizes indicated on a mask sizing ruler that is integrated in a facemask package comprising digitally scanning one or more human faces to obtain one or more images, precisely measuring one or more distances of at least two points on one or more images, categorizing one or more precisely measured distances based on one or more distances of masks of one or more sizes and determining one or more sizes to be indicated on the mask sizing ruler based on categorized one or more precisely measured distances. The method further comprising storing the precisely measured one or more distances in a storage device and processing the distances to categorize into one or more sizes on the sizing ruler.

Other aspects and advantages of the invention will become apparent from the following detail description, taken in conjunction with the accompanying drawings, illustrating by way of example the principles of the invention.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein. Moreover, those in the art will understand that the drawings are not to scale. Wherever possible, like elements have been indicated by identical numbers.

DETAILED DESCRIPTION OF ILLUSTRATIVE EMBODIMENTS

The particular values and configurations discussed in these non-limiting examples can be varied and are cited merely to illustrate at least one embodiment and are not intended to limit the scope thereof.

A facemask package integrated with at least one mask sizing ruler is disclosed. The package stores one or more masks of various sizes. The mask sizing ruler includes a first measuring gauge element, a second measuring gauge element and one or more sizes indicated on the ruler. The sizes in the sizing ruler are determined by categorizing one or more precisely previously measured distances from at least two points on one or more human faces into one or more sizes based on at least one distance on one or more masks of one or more mask sizes. At least one distance on one or more masks of one or more mask sizes is the maximum vertical distance of the mask in folded or unfolded state. A system and method for determining the sizes indicated on the mask ruler are also disclosed. The sizing ruler precisely indicates the size of the mask that most appropriate to a user as the sizes are categorized from the real face dimensions.

Figure 1:
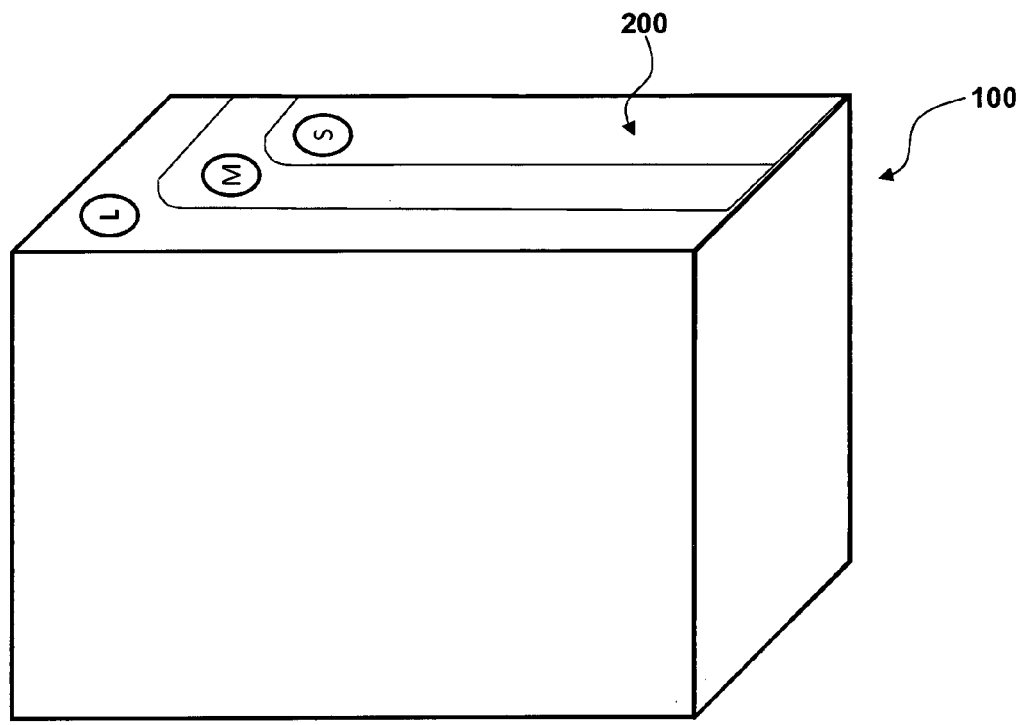
FIG. 1 is an illustration of a perspective view of a facemask package integrated with a mask sizing ruler, in accordance with some embodiments of the disclosed embodiment.

FIG. 1 is an illustration of a perspective view of a facemask package 100 integrated with a mask sizing ruler 200, in accordance with some embodiments of the disclosed embodiment. The package 100 can store one or more masks of one or more sizes. By integrating the mask sizing ruler 200 into the mask package 100, a need for a separate individual mask sizing ruler can be avoided. The ruler 200 can be integrated into a lid or top of the package 100 and hence allows the user to easily take the lid or top and place on the face to determine the most appropriate mask size.

In one embodiment, the ruler 200 can be detachable from the package 100 and can again be attached to the package 100 after use. The sizes indicated on the mask sizing ruler 200 are obtained by precisely measuring one or more facial dimensions of a number of human faces and categorizing all the facial dimensions based on maximum vertical distance of the various sized masks in unfolded state. The package 100 can store masks of single size or various ranges of sizes. Examples of various mask sizes are Mask Small (MS), Mask Medium (MM) and Mask Large (ML) and the ruler can have indication of sizes such as Small (S), Medium (M) and Large (L) that corresponds to MS, MM and ML respectively.

Figure 2:
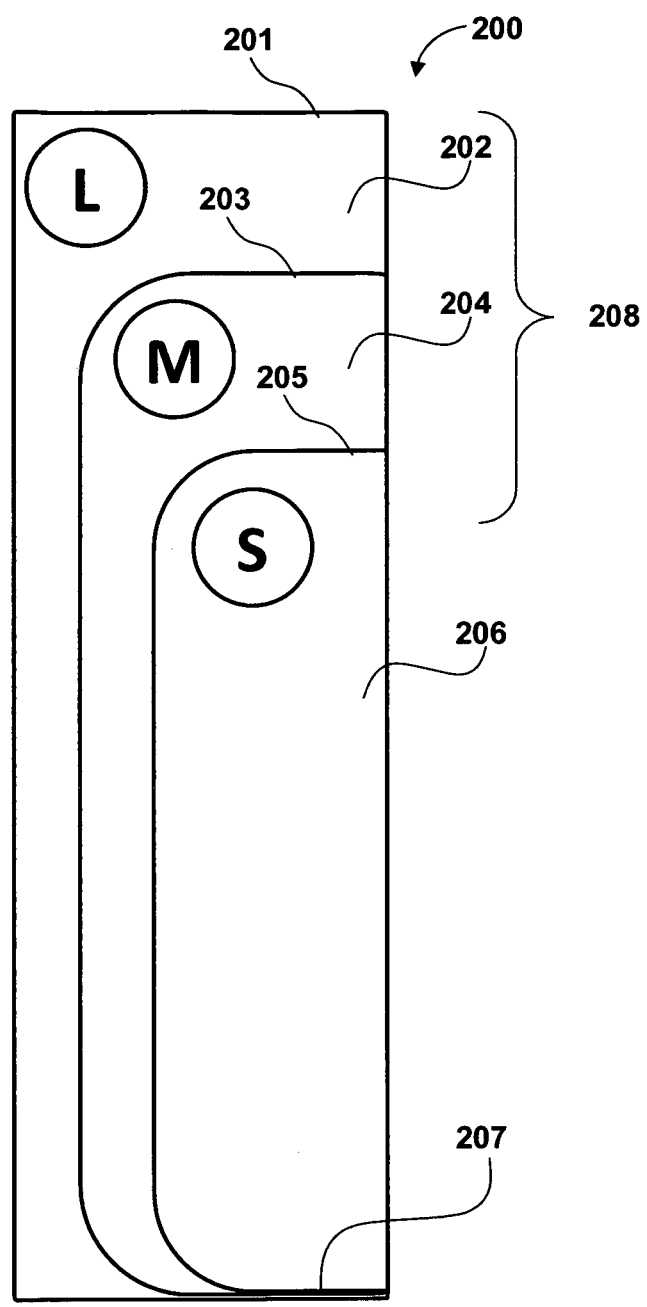
FIG. 2 is an illustration of a side view of the mask sizing ruler depicted in FIG. 1, in accordance with some embodiments of the disclosed embodiment.

FIG. 2 is an illustration of a side view of the mask sizing ruler 200 depicted in FIG. 1, in accordance with some embodiments of the disclosed embodiment. The mask sizing ruler 200 has a first gauge element 207 and a second gauge element 208. The second gauge element 208 is divided into one or more size elements 201, 203 and 205 to form one or more size indicating portions 202, 204 and 206 that indicates the size of the mask that most suits the user. As shown in FIG. 2, the size indicating portions 202, 204 and 206 are formed between the size elements 201, 203, 205 and the first gauge element 207 respectively.

Figure 3:
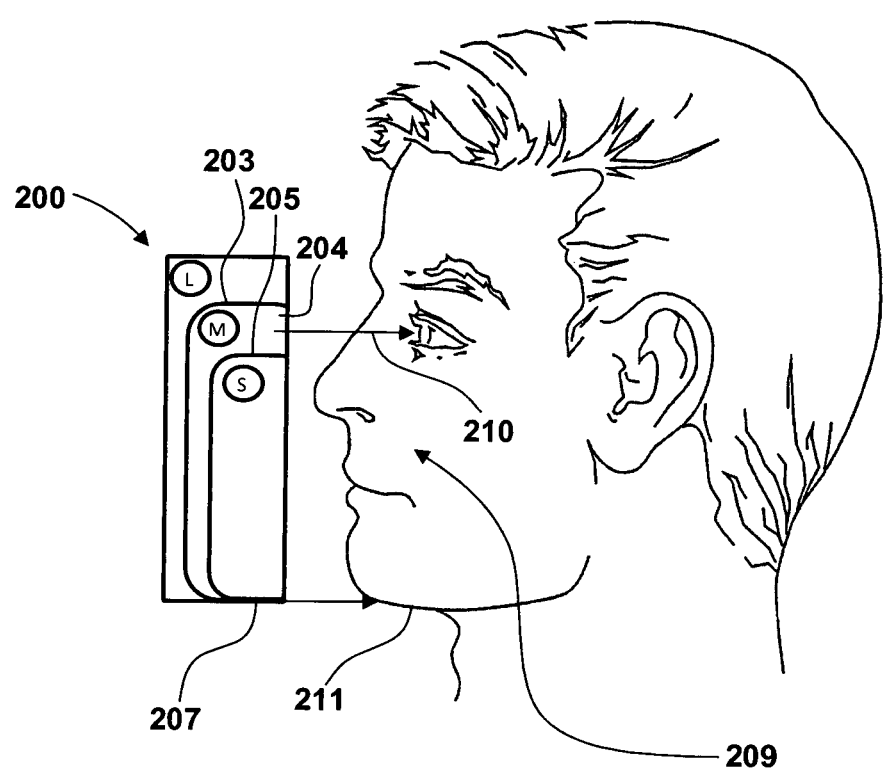
FIG. 3 is an illustration of a schematic diagram of the mask sizing ruler of FIG. 2 utilized for determining the mask size that is appropriate for a human face, in accordance with some embodiments of the disclosed embodiment.

FIG. 3 is an illustration of a schematic diagram of the mask sizing ruler 200 of FIG. 2 utilized for determining the mask size that is appropriate for a human face, in accordance with some embodiments of the disclosed embodiment. As shown in FIG. 3, the first gauge element 207 is placed at, the menton landmark of the face 209, which is the bottom of chin 211. After placing the first gauge element 207 on the user face 209, the size of the mask that most appropriate to the user is directly read at the top. For example, the eye level of the user that corresponds to the size indicating portion of the ruler indicates the mask size of the user. As shown in FIG. 3, the first gauge element 207 is placed at bottom of the chin 211 and the size of the user is determined by reading the size indicating portion 204 that corresponds to the eye level 210 of the user. The size indicating portion 204 indicates size Medium (M) on the ruler 200. The size indicating portions 202, 204 and 206 are formed between the size elements 201, 203, 205 and the first gauge element 207 respectively. While placing the ruler 200 on the face, the eye level of the user always correspond to at least one of the size indicating portions 202, 204 and 206. It should be noted that the size indicating portions 202, 204 and 206 are the sizes, Small (S), Medium (M) and Large (L) on the ruler that corresponds to Mask Small (MS), Mask Medium (MM) and Mask Large (ML) sizes of the mask. The sizes indicated on the ruler is not limited to only Small (S), Medium (M) and Large (L) and can have any number of sizes depending on the available mask sizes.

It should also be noted that the sizes indicated in the ruler is obtained by categorizing one or more precisely previously measured real facial dimensions from at least two points on one or more human faces into one or more sizes based on at least one distance on one or more masks of one or more mask sizes. At least one distance on one or more masks of one or more mask sizes is the maximum vertical distance of the mask in folded or unfolded state. The sizes indicated on the mask ruler are determined by analyzing the real human dimensions and then categorizing the face dimensions based on the mask sizes. Thus, the ruler can substantially precisely indicate the most appropriate size of the mask, as the ruler is based on real human face data.

Figure 4:
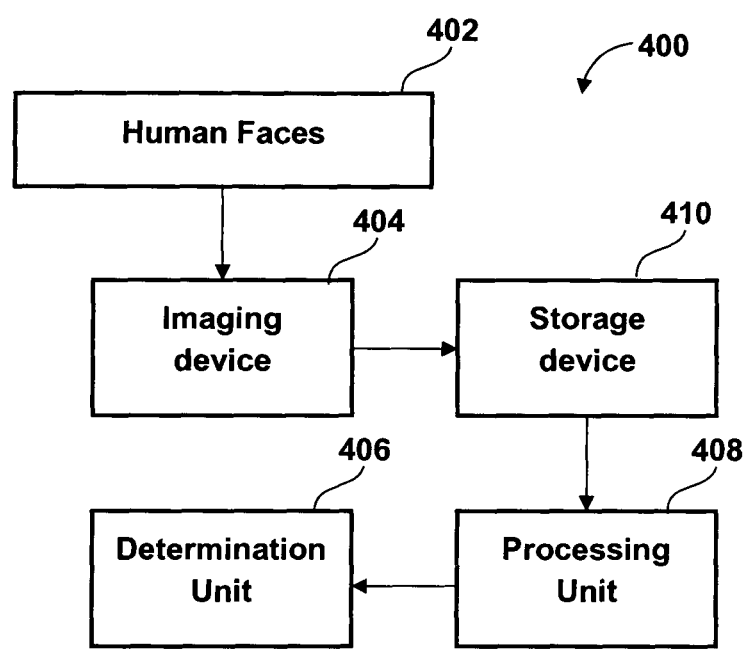
FIG. 4 an illustration a block diagram of a system utilized for detecting the various sizes to be indicated on the mask sizing ruler of FIG. 2, in accordance with some embodiments of the disclosed embodiment.

FIG. 4 an illustration a block diagram of a system 400 utilized for detecting the various sizes to be indicated on the mask sizing ruler 200 of FIG. 2, in accordance with some embodiments of the disclosed embodiments. An imaging device 404 scans one or more human faces 402 to obtain one or more images. The imaging device 404 can be a two or three dimensional scanner, but other imaging devices that are suitable for measuring the facial dimensions of human faces 402 can also be used without limitation. The imaging device 404 can have a processing unit (not shown) and is configured to precisely measure one or more facial distances of at least two points on the images. The two points on human face can be selected from at least one of the following: an eye level, bottom of a chin, a nose bridge, at least one cheek, an end of a lip and a center of a cheek, without limitation. For example, the facial dimensions include the distance from the eye level to the bottom of the chin, the distance of the nose-bridge to the cheek, the distance between the lips, cheek to cheek distance etc., without limitation. It has been found that the largest variation was in the distance from the eye level to the bottom of the chin. Hence, measured distances from the eye level to bottom of the chin are used for determining the sizes to be indicated on the ruler, but other facial dimensions can also be used without limitation.

A storage device 410 stores the precisely measured one or more distances. A processing unit 408 can process the distances to categorize one or more precisely measured distances. For example, the storage device 410 can be a database for storing facial dimensions of one or more faces and the processing unit 408 can have algorithms that can retrieve one or more precisely measured distances from the database and categorize one or more precisely measured distances based on maximum vertical distance of the masks of various sizes. A determination unit 406 determines one or more sizes to be indicated on the mask sizing ruler based on categorized one or more precisely measured distances. It should be noted that the processing unit 408 and determination unit 406 can work as single unit or separate units in coordination and can have algorithms to categorize the measured facial dimensions.

Figure 5:
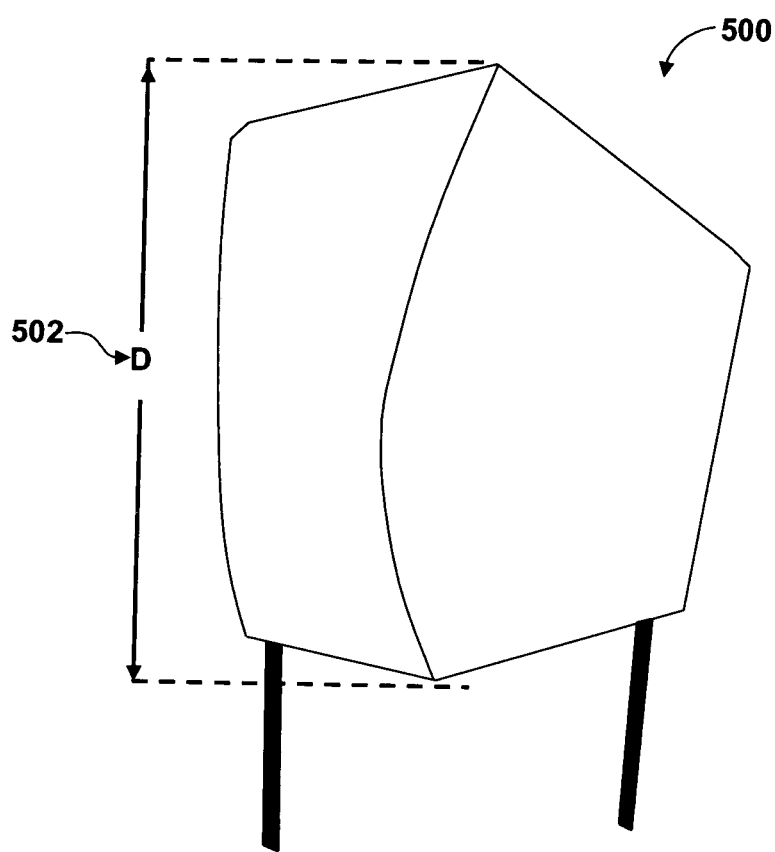
FIG. 5 is an illustration of a side view of a facemask in unfolded state showing the maximum vertical distance, in accordance with some embodiments of the disclosed embodiment.

FIG. 5 is an illustration of a side view of a facemask 500 in unfolded state showing the maximum vertical distance "D" 502, in accordance with the disclosed embodiment. When the facemask is folded, the maximum vertical distance "D" would be increased compared to folded state. The three optimal categorized dimensions form the top three lines of the measuring ruler. These three dimensions are proportional to the maximum vertical distance (D) of the mask in the unfolded state. For example, as shown in FIG. 2, the distance between the size elements 201, 203, 205 and the first gauge element 207 can be proportional to maximum vertical distance of mask of sizes Mask Small (MS), Mask Medium (MM) and Mask Large (ML) respectively. The system 400 depicted in FIG. 4 is utilized for determining the sizes to be indicated on the ruler and the sizes correspond to the maximum vertical distance of the masks of various sizes. It should be noted that the maximum vertical distance of the mask in folded state decreases when unfolded. For example, the optimum chin to eye distance for "M" size is 11.9 cm, and the maximum vertical distance on the mask is 13.9 cm, to account for the reduction in distance when unfolded.

Figure 6:
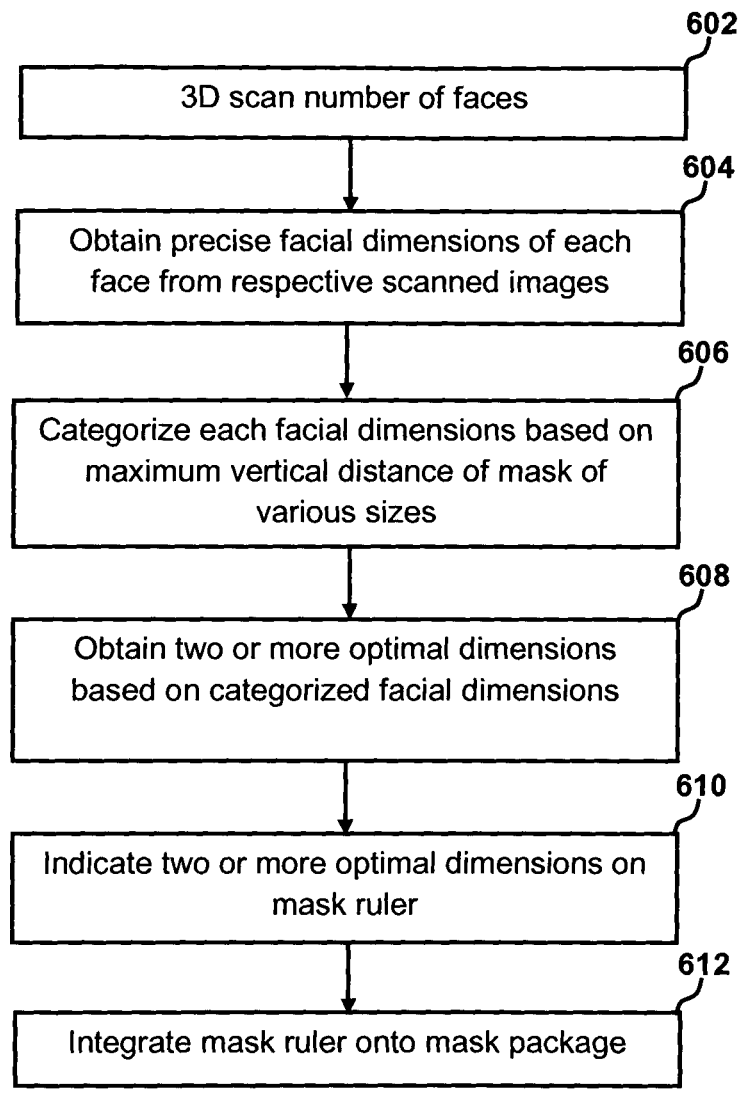
FIG. 6 is an illustration of a flow chart showing a process of determining the mask sizes to be indicated on the mask sizing ruler of FIG. 2, in accordance with some embodiments of the disclosed embodiment.

FIG. 6 is an illustration of a flow chart showing a process of determining the mask sizes to be indicated on the mask sizing ruler of FIG. 2, in accordance with some embodiments of the disclosed embodiment. At block 602 and 604, a number of human faces are scanned by an imaging device for example a 3D scanner and a precise facial dimensions of each face are obtained from respective scanned images. Each facial dimension is categorized based on the maximum vertical distance of mask of various sizes, as illustrated at block 606. At blocks 608 and 610, two or more optimal dimensions based on categorized facial dimensions are obtained and are indicated on the mask ruler. Finally at block 612, the mask ruler indicated with sizes is integrated onto the mask package.

The available mask sizing gauges does not determine the sizes to be indicated on the mask ruler by scanning the human faces and categorizing them based on mask size. Thus, the ruler, system and method in the above embodiments precisely indicate the sizes on the mask ruler and hence the most appropriate mask size of user can be obtained.

It will be appreciated that variations of the above disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Although embodiments of the current disclosure have been described comprehensively, in considerable detail to cover the possible aspects, those skilled in the art would recognize that other versions of the disclosure are also possible.

What is claimed is:

1. A facemask package integrated with at least one mask sizing ruler comprising:
   one or more masks of one or more mask sizes; and
   the mask sizing ruler comprising a first measuring gauge element, a second measuring gauge element,
       wherein the first measuring gauge element is to be placed at the menton landmark of a human face,
       wherein the second measuring gauge element is divided to form two or more size indicating portions measured at the top of the mask size ruler,
       wherein the eye level of the human face corresponds to one of the two or more size indicating portions to indicate the mask size most suited to said human face,
       wherein the two or more size indicating portions are determined by categorizing a plurality of precisely previously measured distances between the menton landmark and the eye level on a plurality of human faces into one or more mask sizes.

2. The facemask package of claim 1, wherein the two or more size indicating portions indicate two or more sizes.

3. The facemask package of claim 1, wherein the first and second measuring gauge elements are used to indicate an appropriate size of a user by placing the mask sizing ruler on the user face and reading the appropriate size.

4. The facemask package of claim 1, wherein said menton landmark of face being the bottom of a chin.

5. The facemask package of claim 1, wherein the second measuring gauge element placed at eye level indicates a size indicated on the sizing ruler.

6. The facemask package of claim 1, wherein one or more mask sizes corresponds to a maximum vertical distance on the mask in folded state or unfolded state.

7. A system of determining one or more sizes indicated on a mask sizing ruler comprising:
   an imaging device configured for scanning a plurality of faces to obtain one or more images and precisely measuring a plurality of distances between a menton landmark and eye level on the plurality of faces on the one or more images;
   a storage device configured for storing the precisely measured plurality of distances;
   a processing unit configured for processing the plurality of distances to categorize the plurality of precisely measured distances in to one or more mask sizes; and
   a determination unit configured for determining one or more sizes to be indicated on the mask sizing ruler based on the categorized plurality of precisely measured distances.

8. The system of claim 7, wherein the one or more mask sizes corresponds to a maximum vertical distance of the mask in folded state.

9. The system of claim 7, wherein the one or more mask sizes corresponds to a maximum vertical distance of the mask in unfolded state.

10. A method of determining one or more sizes indicated on a mask sizing ruler integrated in a facemask package comprising:
    precisely measuring a plurality of distances between a menton landmark and eye level on a plurality of faces;
    categorizing the plurality of precisely measured distances in to one or more mask sizes; and
    determining one or more mask sizes to be indicated on the mask sizing ruler based on the categorized plurality of precisely measured distances.

11. The method of claim 10 further comprising:
    storing the plurality of precisely measured distances in a storage device; and
    processing the plurality of precisely measured distances to categorize into one or more sizes on the sizing ruler.

12. The method of claim 10 further comprising integrating the mask sizing ruler on the facemask package.

13. The method of claim 10, further comprising measuring the plurality of distances between the menton landmark and eye level on the plurality of faces by:
    digitally scanning the plurality of faces to obtain a plurality of face images; and
    obtaining the plurality of distances from the plurality of face images.

14. The method of claim 10, wherein the one or more mask sizes correspond to a maximum vertical distance of the mask in folded state.

15. The method of claim 10, wherein the one or more mask sizes corresponds to a maximum vertical distance of the mask in unfolded state.

* * * * *